United States Patent
Pfrengle et al.

(10) Patent No.: US 6,559,336 B2
(45) Date of Patent: May 6, 2003

(54) PROCESS FOR THE PREPARATION OF 5- AND/OR 6-SUBSTITUTED-2-HYDROXYBENZOIC ACID ESTERS

(75) Inventors: Andreas Pfrengle, Bingen (DE); Robert J. H. Scheffer, Ingelheim (DE); Stefan Scheiblich, Penzberg (DE); Jan Hendrik Wevers, Mainz (DE); Uwe Josef Vogelbacher, Ludwigshafen (DE); Robert F. Doehner, East Windsor, NJ (US)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/975,809

(22) Filed: Oct. 12, 2001

(65) Prior Publication Data

US 2002/0128507 A1 Sep. 12, 2002

Related U.S. Application Data

(63) Continuation-in-part of application No. 09/699,775, filed on Oct. 30, 2000, which is a continuation-in-part of application No. PCT/US00/18768, filed on Jul. 10, 2000, and a continuation-in-part of application No. 09/354,037, filed on Jul. 15, 1999, now abandoned.

(30) Foreign Application Priority Data

Dec. 23, 2000 (WO) ............................. PCT/EP00/13259

(51) Int. Cl.[7] ............................................. C07C 69/88
(52) U.S. Cl. ...................................... 560/67; 568/333
(58) Field of Search .............................. 560/67; 568/333

(56) References Cited

U.S. PATENT DOCUMENTS

| 3,846,497 A | 11/1974 | Himmele |
| 5,773,663 A | * 6/1998 | Curtze |
| 5,945,567 A | 8/1999 | Curtze et al. ................ 568/333 |

FOREIGN PATENT DOCUMENTS

WO          005739     * 1/2001

OTHER PUBLICATIONS

Hauser, F, Synthesis, Georg Thieme Verlag Stuttgard, DE No. 10 Oct. 10, 1980 pp. 814–815.*
Y. Hamada, et al. Tetrahedron, vol. 47, 8635–8652 (1991).
F. M. Hauser, "2–Hydroxy–6–methylbenzoic Acid Derivatives", Synthesis, No. 10, Oct. 1980 pp. 814–815.

* cited by examiner

Primary Examiner—Paul J. Killos
(74) Attorney, Agent, or Firm—Keil & Weinkauf

(57) ABSTRACT

There is provided a single-step process for the preparation of a compound of formula I.

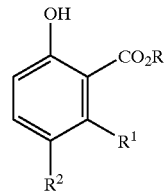

Compounds of formula I are useful as starting materials in the synthesis of natural products and in the manufacture of benzophenone fungicidal agents.

7 Claims, No Drawings

PROCESS FOR THE PREPARATION OF 5- AND/OR 6-SUBSTITUTED-2-HYDROXYBENZOIC ACID ESTERS

This is a continuation-in-part of copending application(s) Ser. No. 09/699,775 filed Oct. 30, 2000, which is a continuation-in-part of international application PCT/US00/18768 filed on Jul. 10, 2000 and a continuation-in-part of U.S. application Ser. No. 09/354,037 filed on Jul. 15, 1999, abandoned; and also claims the benefit under 35 U.S.C. 119 of international application PCT/EP00/13259 filed Dec. 23, 2000, the entire disclosure of which is hereby incorporated by reference.

BACKGROUND OF THE INVENTION

Derivatives of 2-hydroxybenzoic acid esters are useful starting materials for natural product synthesis or for the manufacture of fungicidal benzophenones such as those described in U.S. Pat. No. 5,773,663. Methods to prepare said 2-hydroxybenzoic acid esters are known, i.e. F. M. Hauser, et al., Synthesis 1980, 814 or Y. Hamada, et al, Tetrahedron, Vol. 47 (1991), 8635. However, these known methods require several steps and utilize corrosive or toxic reagents and are not amenable to large scale preparation or commercial manufacturing conditions.

The two-step syntheses cited in Synthesis and Tetrahedron hereinabove require the isolation of intermediates resulting in an undue solvent waste load on the environment. Further these syntheses require gaseous HCl and a separate oxidation procedure employing oxidizing reagents such as $Br_2$ or $CuCl_2$.

Therefore, it is an object of this invention to provide an effective and efficient single-step process to prepare 5- and/or 6-substituted-2-hydroxybenzoic acid esters which is amenable to large scale preparations and commercial manufacturing procedures.

It is another object of this invention to provide an effective means of obtaining a substituted-2-hydroxybenzoic acid ester in good yield under relatively mild reaction conditions from readily available starting materials and reagents.

These and other objects and features of the invention will become more apparent from the detailed description set forth herein below.

SUMMARY OF THE INVENTION

The present invention provides a single-step process for the preparation of a compound of formula I

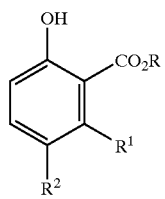

(I)

wherein R is $C_1$–$C_6$alkyl; and
$R^1$ and $R^2$ are each independently H or $C_1$–$C_4$ alkyl which process comprises reacting a compound of formula II

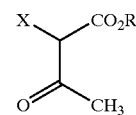

(II)

wherein R is $C_1$–$C_6$alkyl and X is halogen or $OCOCH_3$ with a compound of formula III

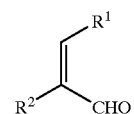

(III)

wherein $R^1$ and $R^2$ are each independently H or $C_1$–$C_4$ alkyl, and formula III compound is understood to be cis, trans, or a mixture thereof, in the presence of a $C_1$–$C_4$carboxylic acid salt and a solvent, wherein the molar ratio of starting materials: compound III to compound II is higher or equal to 1.8.

DETAILED DESCRIPTION OF THE INVENTION

Substituted-2-hydroxybenzoic acid esters of formula I are useful as key starting materials in natural product synthesis and in the manufacture of important benzophenone fungicidal agents. Therefore, the efficient preparation of such fungicidally active compounds in an environmentally sound manner is highly desirable.

The present single-step process makes salicylic acid of the formula I available from β-ketoesters of the formula II and aldehydes of the formula III. Its practicability is ensured by using the aldehyde III in a molar ratio of not less than 1.8 relative to the compound II. This ensures that the reaction mixture remains efficiently stirrable even at low solvent quantities and consistently good yields are obtainable even on an industrial scale.

In a preferred embodiment of the process, the aldehyde III is initially charged and subsequently the salt and the solvent are added in succession or concurrently in the course of generally 0 to 3 hours.

It can further be of advantage to raise the reaction temperature in the course of the reaction from initially 60–120° C. to finally 130–140° C.

Preferred compounds prepared by the process of the invention are those compounds of formula I wherein $R^1$ is $C_1$–$C_4$ alkyl and R is hydrogen. More preferred compounds are those compounds of formula I wherein $R^1$ is methyl and $R^2$ is hydrogen.

Preferred compounds of formula II employed in the process of the invention are those compounds wherein X is halogen. More preferred compounds are those compounds of formula II wherein X is Cl.

Compounds of formula III may be represented in the cis or trans configuration or as a mixture thereof. In the specification and claims, compounds designated as formula III include the cis isomer, the trans isomer or a mixture therof.

The term halogen as used in the specification and claims designates Cl, Br, F or I.

In accordance with the process of the invention, a β-ketoester of formula II is reacted with an α,β-unsaturated aldehyde of formula III in the presence of a $C_1$–$C_4$ carboxylic acid salt and a solvent to form the desired product of formula I. The reaction is shown in flow diagram I wherein M is an alkali metal or an alkaline-earth metal Flow Diagram I

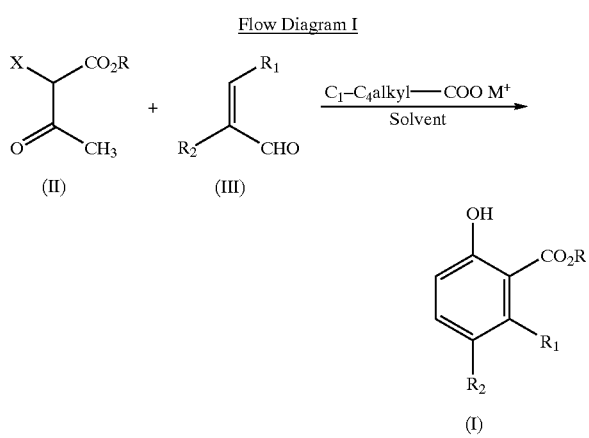

Suitable solvents for use in the inventive process include polar solvents, preferably protic solvents such as $C_1$–$C_4$ carboxylic acids or $C_1$–$C_6$ alkanols. Preferred solvents are $C_2$–$C_4$ carboxylic acids or mixtures of a $C_2$–$C_4$ carboxylic acid and a $C_1$–$C_6$ alkanol, more preferably acetic acid or a mixture thereof with methanol or ethanol. In general, more than 2.5 molar equivalents of solvent; preferably about 2.5 to 5 and more preferably about 2.5 to 3.5 molar equivalents of solvent were used.

Acid salts suitable for use in the process of the invention are $C_1$–$C_4$ carboxylic acid alkali metal or alkaline-earth salts, more preferably acetic acid alkali metal salts such as sodium acetate or potassium acetate. Preferably about 1.3 to 3.0 molar equivalents, more preferably about 1.4 to 1.6 molar equivalents of the carboxylic acid salt were added to the reaction mixture.

In the present process, the aldehyde III is used in a molar ratio of not less than 1.8 relative to the compound II. Preferably about 1.9 to 2.5 and more preferably about 2.0 to 2.2 molar equivalents of aldehyde III were reacted.

In a preferred embodiment of the process, the aldehyde III is initially charged and subsequently the salt and the solvent are added in succession or concurrently in the course of generally 0 to 3 hours. It can be of advantage here first to add a portion or the total amount of the salt and only then to start with the addition of the solvent. Compound II is generally added last in the course of 0 to 3 hours.

In the process of the invention, reaction rate is directly related to reaction temperature, that is, the reaction rate increases with increased temperature. However, excessively high reaction temperatures may lead to decomposition and the formation of undesired by-products, thereby reducing product yield and purity. Suitable reaction temperatures in the process of the invention may range from room temperature to the reflux temperature of the solvent preferably about 60° C. to 150° C., more preferably about 110° C. to 140° C.

It can further be of advantage to raise the reaction temperature in the course of the reaction from initially 60–120° C. to finally 130–140° C. The reaction temperature can be raised for example by removing low boilers, if necessary by applying reduced pressure. It is similarly possible to carry out the reaction in a closed system. In this case, a higher reaction temperature will automatically result in a higher pressure. The pressure employed is preferably in the range from 0.1 to 6 atm.

The individual reactants are generally added at room temperature to the reflux temperature of the solvent.

The reaction time is generally in the range from 3 to 8 hours.

The formula I hydroxybenzoic acid ester product may be isolated using conventional isolation techniques such as precipitation, decantation, filtration, extraction, chromatographic separation or the like, preferably filtration or extraction.

Compounds of formula I are useful as intermediates in the synthesis of natural products in the manufacture of benzophenone fungicidal agents as described in U.S. Pat. No. 5,773,663.

For a more clear understanding of the invention, the following example is set forth below. This example is merely illustrative and is not to be understood as limiting the scope or underlying principles of the invention in any way.

The term NMR designates nuclear magnetic resonance spectroscopy. Unless otherwise mentioned, all parts are parts by weight.

EXAMPLE 1

Preparation of Ethyl 2-Hydroxy-6-methylbenzoate

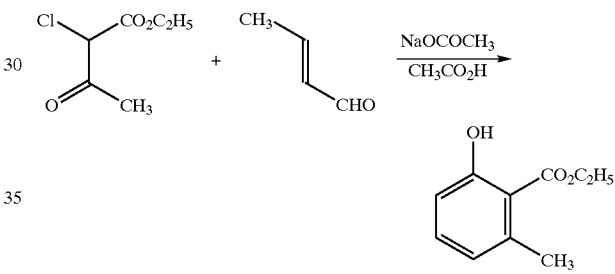

A 4 liter jacketed vessel fitted with a destination apparatus was initially charged with 770.9 g [11 mol] of crotonaldehyde. With stirring, 615.2 g [7.5 mol] of anhydrous sodium acetate were added and the batch was heated to 60° C. 900 g of acetic acid were then metered in over an hour, during which the temperature rose to 83° C. The suspension was then heated under reflux and admixed with 857.2 g [5 mol] of ethyl 2-chloroacetate (purity: 96%) in the course of an hour.

The batch was subsequently stirred for five hours, during which initially about 700 ml of low boilers were destined off until an internal temperature of 130° C. was attained. The pressure was then reduced to 200 mbar and the distallation continued until the internal temperature again reached 135° C.

The residue was cooled down to 85° C. and admixed with 1250 g of water (preheated to 80° C.). After 10 min of stirring at 80° C. the aqueous phase was separated off. This afforded 893 g of organic phase as a dark brown oil having a product content of 63.2% (which corresponds to a yield of 62.6% of theory).

We claim:
1. A process for the preparation of a compound of formula I

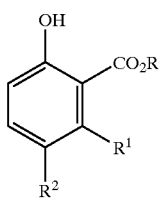

(I)

wherein R is $C_1$–$C_6$ alkyl; and $R^1$ and $R^2$ are each independently H or $C_1$–$C_4$ alkyl which process comprises reacting a compound of formula II

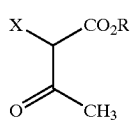

(II)

wherein R is $C_1$–$C_6$ alkyl and X is halogen or $OCOCH_3$ with a compound of formula III

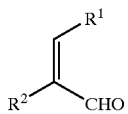

(III)

wherein $R^1$ and $R^2$ are each independently H or $C_1$–$C_4$ alkyl, in the presence of a $C_1$–$C_4$ carboxylic acid salt and a solvent, wherein the molar ratio of compound III compound II is higher or equal to 1.8.

2. The process according to claim 1 wherein the aldehyde III is initially charged, the salt and the solvent are subsequently added in succession or concurrently and finally compound II is added.

3. The process according to claim 1 wherein a reaction temperature of initially 60° C. to the reflux temperature of the solvent used is set and the temperature is raised to 130–140° C. in the course of the reaction.

4. The process according to claim 1 wherein the solvent is a $C_1$–$C_4$ carboxylic acid or a mixture thereof with a $C_1$–$C_6$ alkanol.

5. The process according to claim 2 wherein the solvent is acetic acid and the $C_1$–$C_4$ carboxylic acid salt is sodium acetate.

6. The process according to claim 1 having a formula II compound wherein X is Cl.

7. The process according to claim 1 having a formula III compound wherein $R^1$ is methyl and $R^2$ is H.

* * * * *

UNITED STATES PATENT AND TRADEMARK OFFICE
CERTIFICATE OF CORRECTION

PATENT NO.    : 6,559,336 B2                                    Page 1 of 1
DATED         : May 6, 2003
INVENTOR(S)   : Pfrengle et al.

It is certified that error appears in the above-identified patent and that said Letters Patent is hereby corrected as shown below:

Column 6,
Line 3, "compound III compound II" should be -- compound III:compound II --.

Signed and Sealed this

First Day of July, 2003

JAMES E. ROGAN
*Director of the United States Patent and Trademark Office*